United States Patent [19]

Oberhardt

[11] 4,288,228

[45] Sep. 8, 1981

[54] WHOLE BLOOD ANALYSES AND DIFFUSION APPARATUS THEREFOR

[75] Inventor: Bruce J. Oberhardt, Katonah, N.Y.

[73] Assignee: Technicon Instruments Corporation, Tarrytown, N.Y.

[21] Appl. No.: 7,858

[22] Filed: Jan. 31, 1979

[51] Int. Cl.³ .................. G01N 31/06; G01N 33/52
[52] U.S. Cl. .................. 23/230 R; 23/230 B; 422/56; 422/69
[58] Field of Search .................. 23/230 R, 230 B; 422/56, 58, 66, 69; 195/103.5 R; 435/299, 301, 805, 27, 25, 26

[56] References Cited

U.S. PATENT DOCUMENTS

| 3,146,163 | 8/1964 | Brewer | 195/103.5 R |
|---|---|---|---|
| 3,368,872 | 2/1968 | Natelson | 422/66 |
| 3,511,608 | 5/1970 | Anderson | 422/56 |
| 3,526,480 | 9/1970 | Findl et al. | 422/66 |
| 3,607,093 | 9/1971 | Stone | 435/299 X |
| 3,791,930 | 2/1974 | Saxholm | 195/103.5 R |
| 3,798,004 | 3/1974 | Zerachia et al. | 422/56 |
| 3,891,776 | 9/1976 | Saxholm | 422/69 X |
| 3,901,657 | 8/1975 | Lightfoot | 422/56 |
| 3,990,849 | 11/1976 | Lee et al. | 23/230 B |
| 4,069,017 | 1/1978 | Wu et al. | 422/56 X |

FOREIGN PATENT DOCUMENTS 2416047 10/1975 Fed. Rep. of Germany ........ 422/56

Primary Examiner—Arnold Turk
Attorney, Agent, or Firm—S. P. Tedesco

[57] ABSTRACT

Methods and apparatuses are featured for analyzing whole blood samples by diffusion techniques in porous media. A fluid component of the whole blood is diffused into a thin-film porous medium of a given predetermined volume. Hematocrit dependent errors in diffusion time do not pose a problem in obtaining a precise aliquot of the fluid component of the whole blood due to rapid diffusion and saturation of the fluid component into the porous medium.

In another embodiment, diffusion switches or valves allow for precise aliquots in porous media by control of the diffusion and/or reaction of sample analyte with reagents.

31 Claims, 24 Drawing Figures

WHOLE BLOOD ANALYSES AND DIFFUSION APPARATUS THEREFOR

FIELD OF THE INVENTION

The invention relates to whole blood testing and, more particularly, to obtaining an aliquot of a fluid component of the whole blood sample by diffusion into a porous medium.

BACKGROUND OF THE INVENTION

Many techniques for analyzing whole blood samples have been proposed in the prior art. In some prior art methods, the fluid components are separated from the red blood cells (hematocrit) by first filtering the whole blood sample through a porous medium, such as a layer of cellulose. The red blood cells are trapped on top of the filter. The fluid components passing through the filter are then deposited upon a tape or other medium containing a reagent for testing the fluid sample for a particular component such as: glucose, BUN, $Na^+$, etc. Such techniques may be seen with reference to U.S. Pat. Nos. 3,260,413, issued July 12, 1966, and 3,261,668, issued July 19, 1966.

In the above methods, the object of the invention is to perform rapid analyses of the blood samples in an automated fashion, using a minimum of sample volume, e.g., 20 microliters. While such techniques are generally useful for their intended purposes, they are not totally successful. This is because each filtered fluid sample must be carefully metered to obtain an aliquot. When dealing with small quantities of fluid such as 20 microliters, even a small error in sample volume will give a totally erroneous result.

It has been realized, therefore, that a major problem in the automated analysis of whole blood could be eliminated by obtaining an accurate aliquot of sample in a simple and convenient manner.

In the U.S. patent application to Martin J. Lee, Ser. No. 922,611, filed July 7, 1978, assigned to a common assignee, it has been proposed that an aliquot of a blood analyte could be obtained by diffusion of the blood analyte from a serum sample into a gel or other porous medium for a given period of time. This approach, therefore, suggests a measurement of time in contrast to previous sample volume metering. Accurate time measurements are easier to achieve than sample volume measurements. However, if whole blood is used, the diffusion of fluid components are dependent upon factors other than time. For example, a correction factor is needed to account for changes in diffusion rates resulting from variations in hematocrit from sample to sample, i.e., each whole blood sample has a different amount of red blood cells which alters the diffusion rate of fluid diffusing into the porous medium. (See U.S. patent application to Martin J. Lee and Michael J. Malin, Ser. No. 936,436, filed Aug. 24, 1978, now U.S. Pat. No. 4,250,257, assigned to a common assignee.)

In one embodiment of the present invention, this previous problem is overcome by obtaining an accurate aliquot using a method which is neither time nor hematocrit dependent. The invention seeks to provide a thin film of gel or other porous material having a known predetermined volume. When a drop of whole blood is deposited on the gel, it will equilibrate or otherwise diffuse to saturation almost immediately, due to the minute volume and thin-layer geometry of the gel. In other words, rather than meter the sample to obtain an aliquot, this embodiment of the invention controls the volume of the receptacle into which the sample is diffused. The manufacture of precise gel volumes can be easily controlled, thus providing for automation of whole blood sample analyses which are accurate, rapid, and convenient.

In other embodiments of the invention, a timed diffusion is more accurately achieved than disclosed by the prior art, through the use of a molecular diffusion switch or valve. The molecular diffusion switch comprises an impermeable barrier disposed between two porous media across which diffusion is to occur. The impermeable barrier is removed and then restored, such that the diffusion across the media is precisely time controlled. In a preferred arrangement, the impermeable barrier is an immiscible fluid interposed between the two porous media containing diffusable species. The impermeable barrier fluid is easily displaced from between the media and then restored therebetween, to achieve the objective of controlling precisely the initiation and duration time of diffusion between the two porous media to provide an accurate aliquot.

SUMMARY OF THE INVENTION

The invention pertains to methods and apparatuses for rapidly obtaining an aliquot of a fluid component of a whole blood sample. In a first embodiment, a precise aliquot is obtained by diffusing said fluid component into a given predetermined volume of thin-film porous medium. The whole blood sample is made to contact the surface of the thin-film porous medium. At least a portion of a fluid component is allowed to diffuse into the porous medium until saturation.

Analysis of the fluid component is achieved by removing the excess sample from the surface of the porous medium and then contacting this component containing medium with a reagent containing medium. After allowing for cross-diffusion between the media, the reaction between the fluid component and the reagent is measured in either medium.

In another embodiment of the invention, a precise aliquot is obtained by a carefully controlled cross-diffusion between the porous media via a molecular diffusion switch. The molecular switch achieves accurately timed diffusion of substances from one medium to another, such that an amount (aliquot) of material may be accurately and precisely transferred. The molecular switch is comprised of an impermeable layer which acts as a barrier or isolating means between two porous media. Preferably, this impermeable layer is an immiscible fluid (i.e., gas or liquid) which is easily displaced from between the porous media, and then restored therebetween.

For example, where the diffusable substance(s) is in an aqueous solvent, a hydrophobic substance may be used as an immiscible barrier liquid. Where the diffusable substance(s) are hydrophobic, a hydrophilic substance may be utilized as a barrier liquid.

It is an object of this invention to provide improved methods and apparatuses for analyzing a whole blood sample;

It is another object of the invention to provide methods and apparatuses for obtaining an aliquot of a fluid component of a whole blood sample in a rapid, expeditious manner;

It is a further object of this invention to provide a method and apparatus for obtaining an aliquot of a fluid component of a whole blood sample by diffusion of the fluid component into a given volume of a porous medium;

It is still another object of the invention to provide a method for obtaining an aliquot of a fluid component of a whole blood sample by time independent diffusion techniques;

It is still a further object of this invention to provide improved means for accurately controlling the diffusion of a substance between two media;

It is still another object of the invention to provide an improved means of obtaining an aliquot of a substance by timed diffusion techniques.

These and other objects of this invention will be better understood and will become more apparent with reference to the following detailed descriptions taken in conjunction with the accompanying drawings, in which:

DETAILED DESCRIPTION

Generally speaking, the description of this invention will focus upon whole blood analysis as a vehicle to explain and clarify the inventive concepts. However, it is to be understood that such description is only by way of example, and is not meant to limit the scope and spirit of the invention which is meant to be defined by the appended claims.

Figure 1A:
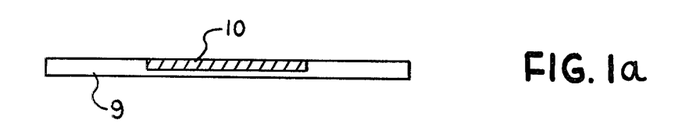
FIGS. 1a through 1e are sectional sequential views of one embodiment of the blood analyzing invention.
Figure 1B:
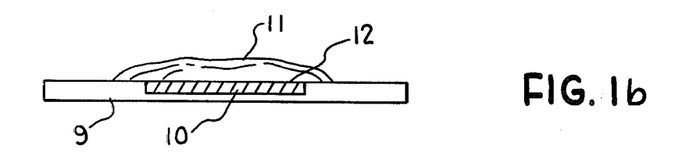

Now referring to FIGS. 1a through 1f, a first embodiment of the invention is illustrated. FIG. 1a shows a transparent substrate 9 supporting a porous medium 10 of a given predetermined volume. The medium 10 can be an aqueous gel in the case of blood analysis. A drop of blood 11 to be analyzed is placed over gel 10 in surrounding overlapping fashion as shown in FIG. 1b. The plasma of the whole blood penetrates and completely saturates the gel 10 almost immediately because the gel 10 is very thin and has a very small volume. An accurate aliquot of the plasma is obtained because of the known volume of the gel. This volume is accurately controlled in manufacture.

The pore size of the porous medium 10 is selected to exclude red blood cells (hematocrit) and other large blood proteins. Hematocrit effects do not pose a problem in obtaining the plasma aliquot, because saturation of gel 10 is almost instantaneous.

Figure 1C:
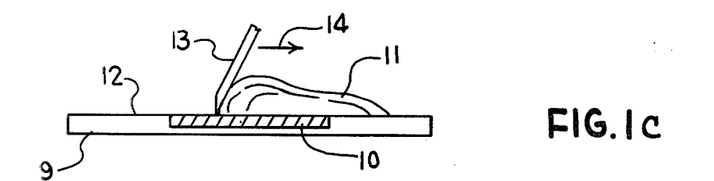

After the gel 10 has been saturated with the plasma from blood sample 11, the remaining sample 11 is removed from the surface 12 of gel 10 and substrate 9. There are several ways to accomplish this, as will be described with reference to FIGS. 1c, 1f, 3 and 3a. In FIG. 1c, the blood remainder is being removed by a squeegee or wiper blade 13, which is drawn across the surface 12 (arrow 14).

Figure 1D:
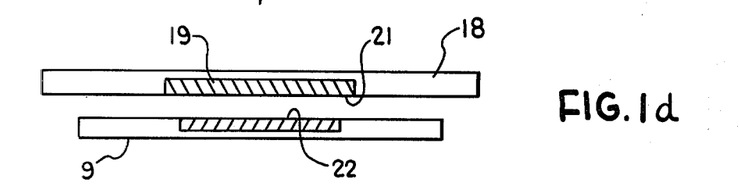
Figure 1E:
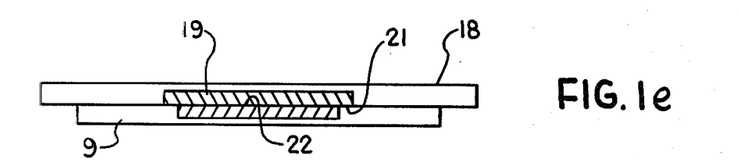
Figure 1F:
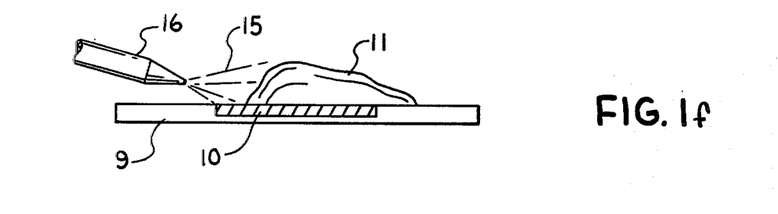
FIG. 1f is a sectional view of an alternate embodiment to the method step illustrated in FIG. 1c.

Another way of removing the blood remainder involves a wash or jet-air-spray 15 shown in FIG. 1f. A nozzle 16 can dispense a high pressure air spray or a hydrophobic spray wash 15 (where an aqueous sample such as blood is used). Care is taken not to draw any of the plasma out of gel 10.

Figure 3:
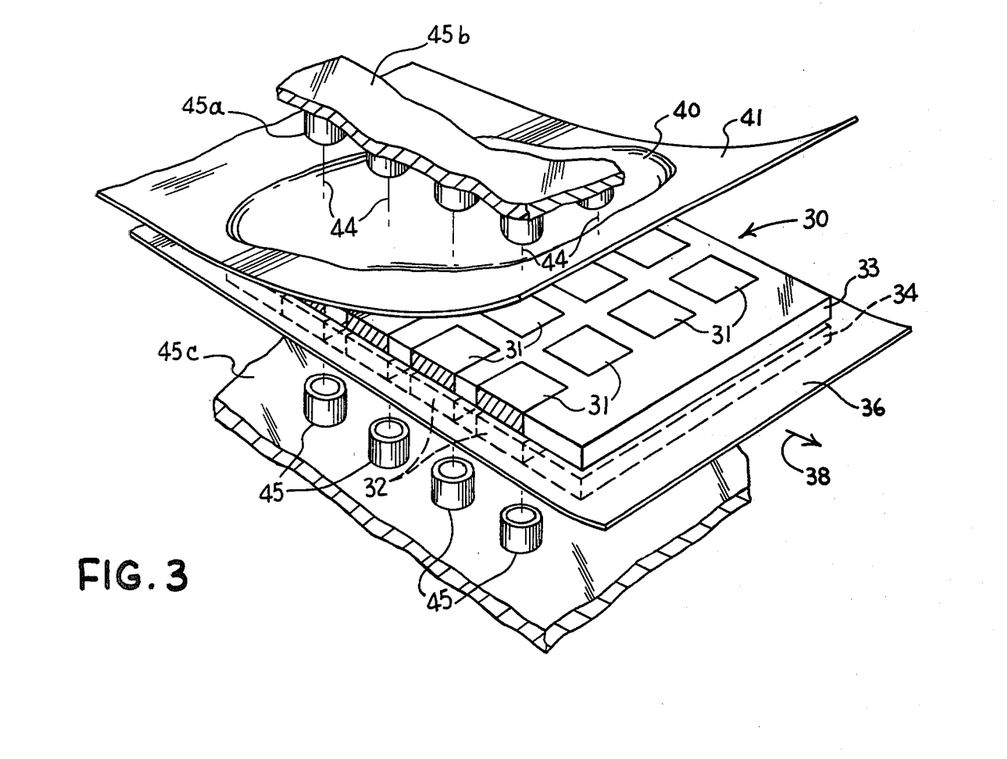
FIGS. 3 and 3a are perspective cut-away views of an alternate embodiment of the inventive apparatus shown in FIG. 2.
Figure 3A:
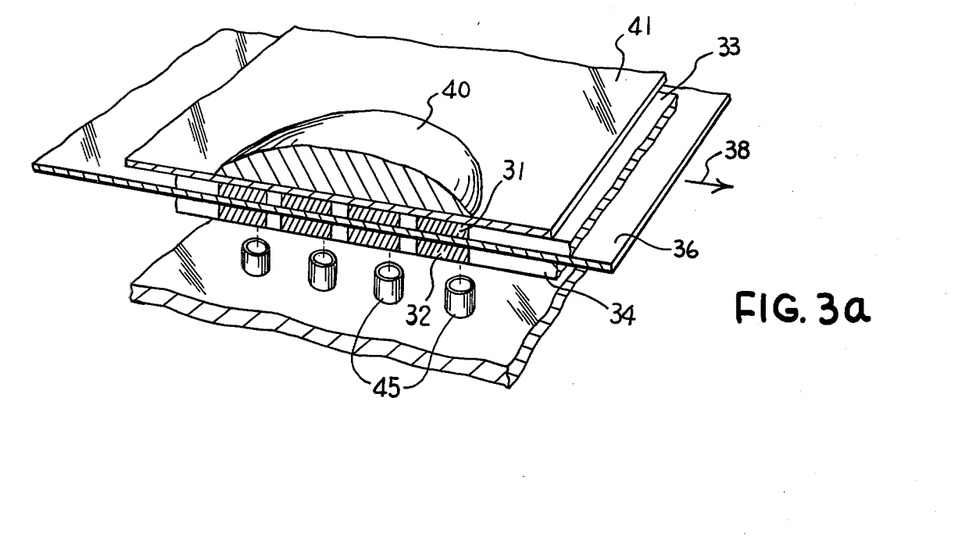

In FIGS. 3 and 3a, another method is shown for removal of the blood sample by means of a peel-away layer as will be discussed hereinafter.

Analysis of one of various analytes or components of the plasma is achieved by reacting the desired analyte with a reagent(s) of known concentration, and observing a color change.

FIG. 1d illustrates a second transparent substrate 18 supporting a second gel or porous medium 19. Porous medium 19 contains the reagent(s) needed to produce a reaction (e.g., color change) with the desired analyte to be analyzed.

Substrates 9 and 18 are brought together (arrow 20) so that contact is achieved between gel surfaces 21 and 22 as illustrated in FIG. 1e. When the gels 10 and 19 are in contact, cross diffusion of analyte and reagent will occur across the boundary defined by gel surfaces 21 and 22.

One method for measurement is to produce a color by the reaction of analyte and reagent, which is detected and analyzed by directing a light beam through gels 10 and 19 to a colorimeter detector (not shown).

Figure 2:
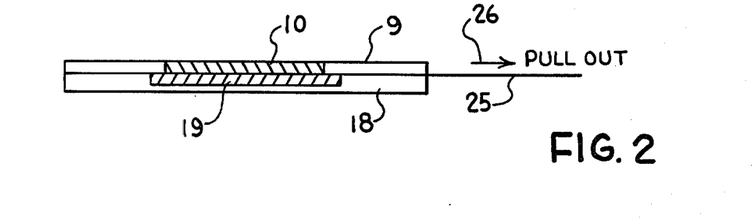
FIG. 2 is a sectional view of an alternate embodiment of the invention depicted in FIGS. 1a through 1e.

A second embodiment of the invention is shown in FIG. 2. In this embodiment, substrates 9 and 18 are constructed in contiguous fashion as illustrated with a thin impermeable layer 25 disposed therebetween. Procedures of FIGS. 1a through 1c are carried out just as before. When a reaction between the analyte and reagent is to be initiated, the impermeable layer 25 is removed (extracted) from between gels 10 and 19 are depicted by arrow 26. This establishes diffusion of sample from gel 10 to gel 19. Again, development of color may be utilized to quantitate the analyte in the sample.

FIGS. 3 and 3a illustrate a perspective view of an array 30 of gels 31 and 32 having common substrates 33 and 34, respectively. This array 30 has a similar construction as the single analyte analyzing device shown in FIG. 2. An impermeable barrier 36 is disposed between substrates 33 and 34 to prevent reaction between respective reagents in gels 32 with the analytes in gels 31.

The array 30 is designed to analyze a plurality of sample analytes simultaneously. Each gel 32 has a reagent(s) specific for only one analyte of the plasma contained in gels 31.

Plasma is introduced to the gels 31 in a slightly different way then previously described. A whole blood sample 40 (FIG. 3a) is deposited on top of a porous layer 41, which absorbs the plasma of the blood sample 40 while screening out the blood cells. The plasma is allowed to filter through layer 41, and diffuse into thin layered gels 31. As before, the saturation of gels 31 is almost accomplished instantaneously. When the plasma is within the gels 31, the porous layer 41 is peeled from substrate 33, thus removing the remaining blood portion. Next, the impermeable layer 36 is removed from between gels 31 and 32 and substrates 33 and 34, as depicted by arrow 38. After cross diffusion of analyte and reagent in corresponding gel pairs 31 and 32 takes place, a light beam 44 emitted from source 45a contained on substrate (plateform) 45b is directed through each gel pair 31, 32 to a respective colorimeter detector 45 contained on substrate (platform) 45c. Several analytes from a sample can thus be simultaneously analyzed by this apparatus.

Referring to FIGS. 4a through 4f, another embodiment of the invention is illustrated. This embodiment features two or more circular porous layers or membranes 50a, 50b, 50c, etc., joined at the periphery by an inert, non-porous spacer 55. The first membrane 50a receives the blood sample on its surface 51, similar to the other embodiments. The membranes 50b and 50c can contain a reagent for reaction with an analyte of the blood sample that has diffused into layer 50a.

Figure 4A:
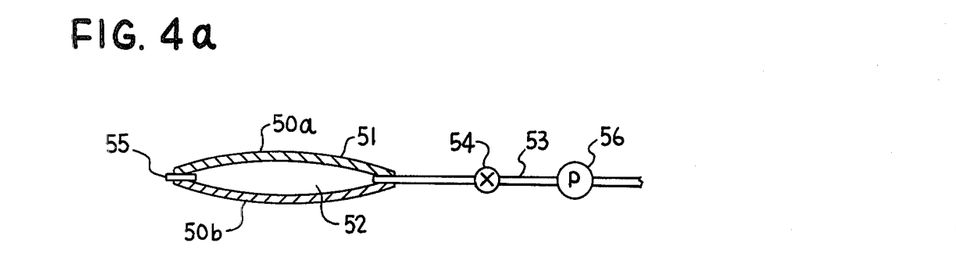
FIGS. 4a, 4b and 4d through 4f are sequential illustrations of sectional views of an alternate embodiment for the inventive apparatus set forth in FIGS. 1a through 1e.
Figure 4B:
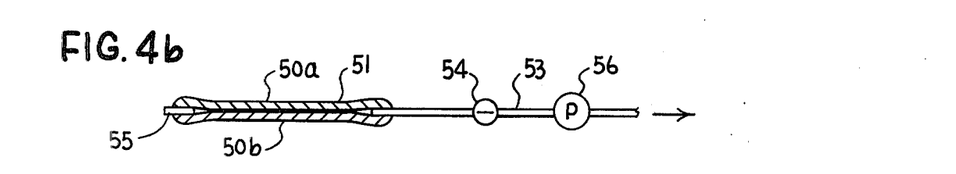
Figure 4C:
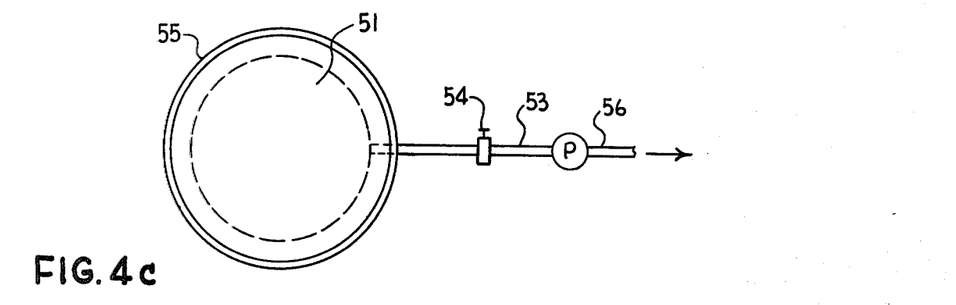
FIG. 4c depicts a top view of the apparatus shown in FIGS. 4a, 4b or 4d through 4f.
Figure 4D:
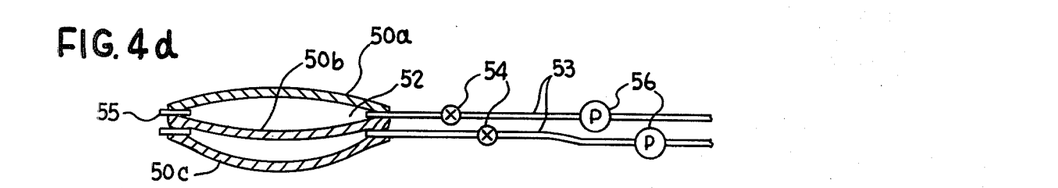

Initially, a cavity 52 exists between layers 50a and 50b as in FIG. 4a, or between layers 50a and 50b, and 50b and 50c, as shown in FIG. 4d. Cavity 52 can be filled with air or with a barrier liquid, as will be explained hereinafter. Each cavity 52 communicates with a duct 53 containing a valve 54. A reversible pump 56 is disposed in each duct 53 to withdraw or inject fluid from and into each respective cavity 52.

Figure 4E:
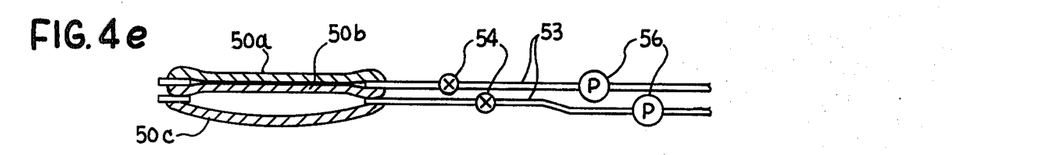

As aforementioned, the surface 51 of layer 50a is covered with a whole blood sample until layer 50a is completely saturated with the plasma of the sample. Next, the remaining blood portion on surface 51 is removed, and layers 50a and 50b are brought into contact as shown in FIGS. 4b and 4e. This contact is accomplished by evacuating the cavity 52 between layers 50a and 50b. The valve 54 disposed in respective ducts 53 is opened and the pump 56 pumps out the air or barrier fluid in cavity 52.

Figure 4F:
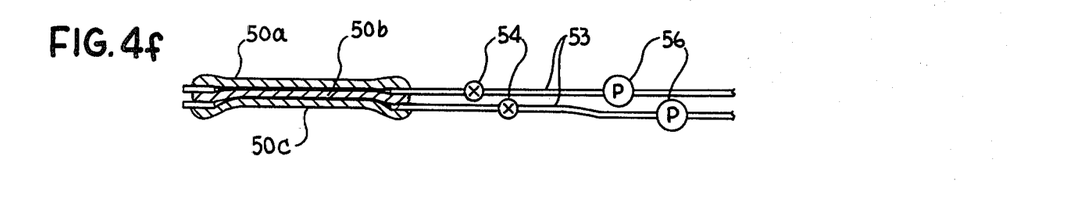

The contacting layers 50a and 50b now allow cross diffusion of the sample analyte and the reagent. If desired, an additional reagent in layer 50c may be sequentially diffused and reacted with the products of the first reaction, by similarly evacuating the cavity 52 between layers 50b and 50c, as shown in FIG. 4f.

In some cases, it may be desirable to halt diffusion or to allow diffusion of the reactants for a given time period. In such a method, the air or liquid may be pumped back into cavity 52 after a given time interval.

Figure 5A:
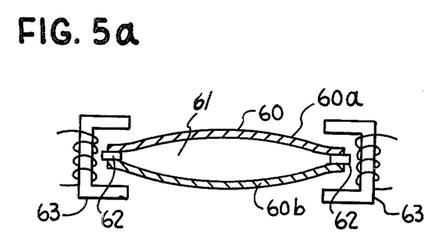
FIGS. 5a and 5b are sectional sequential views of still another embodiment of the invention shown in FIGS. 1a through 1e.
Figure 5B:
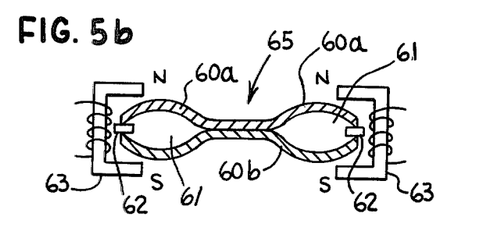

Referring now to FIGS. 5a and 5b, still another embodiment of the invention is depicted. This embodiment features two porous hydrophilic membrane or gel layers 60a and 60b, normally separated by a magnetic fluid 61 which is hydrophobic (FIG. 5a). As before, the whole blood sample (not shown) is spread upon surface 60 of layer 60a, and the plasma of the blood sample is allowed to diffuse into, and saturate, porous layer 60a. The remaining blood fraction disposed on surface 60 is then removed. Having saturated layer 60a, the plasma analytes to be determined are desired to be reacted with color producing reagent(s) contained in layer 60b. The reaction between analyte and reagent is accomplished by bringing layers 60a and 60b into contact so that cross-diffusion of the reactants may occur, as illustrated in FIG. 5b. Until such contact is achieved, the hydrophobic magnetic fluid 61 prevents any meaningful diffusion from taking place between the layers 60a and 60b. The magnetic fluid 61 acts as a barrier layer between layers 60a and 60b.

Layers 60a and 60b can be circular in shape, and may be joined at the periphery by an annular, inert non-porous spacer 62. At the periphery are located electromagnets 63, which when energized, as shown in FIG. 5b, will attract the magnetic fluid 61 and cause the magnetic fluid 61 to concentrate at the periphery by the layers 60a and 60b. As magnetic fluid is displaced in the center portion, layers 60a and 60b will contact each other, as illustrated. Cross-diffusion will now be achieved, and a color will be developed in the center area 65. The color development will be indicative of the analyte (under test) in the fluid sample. The color can be read by standard colorimetric or spectrophotometric techniques, as previously mentioned.

Figures 6A, 6B, 7C:
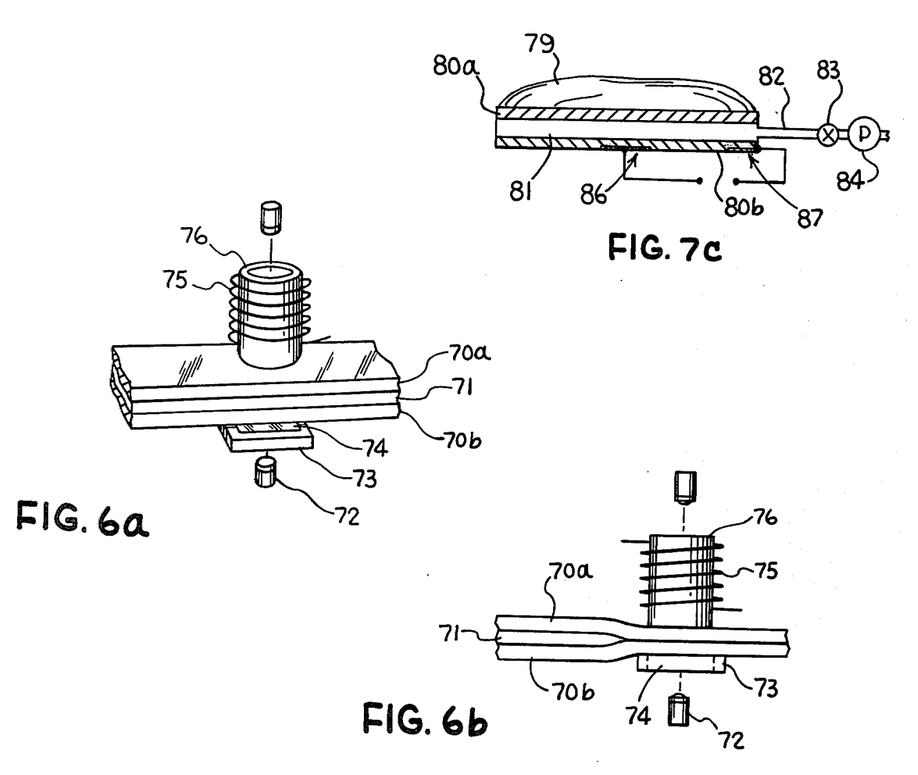
FIG. 6a is a perspective view of yet a further embodiment of the invention depicted in FIGS. 1a through 1e.
FIG. 6b is a sectional view of FIG. 6a shown in an operative position.
FIGS. 7a through 7c are sectional sequential views of but another embodiment of the apparatus illustrated in FIGS. 1a through 1e.

FIGS. 6a and 6b illustrate a further embodiment of the invention. Two porous hydrophilic membranes or gels 70a and 70b, each respectively containing a sample analyte and a reagent are again separated by a hydrophobic liquid barrier layer 71 (FIG. 6a). Layers 70a and 70b may be circular in shape and attached at their periphery to an annular, inert, non-porous spacer (not shown). An annular (e.g., rectangular frame) magnetizable ring 73 peripherally surrounds and supports a rigid transparent plate 74 which, in turn, supports layer 70b. A magnetic coil 75 wrapped around a hollow magnetizable tube 76 is disposed on the top of layer 70a. When the coil 75 is energized, the ring 73 will cause the plate 74 to push against layer 70b. This will result in bringing layers 70a and 70b into contact with each other and displace liquid 71, as shown in FIG. 6b.

Light can be projected through the hollow tube 76, and through layers 70a, 70b and transparent plate 74 to a colorimeter detector 72. Thus, the developing color between reagent and analyte will be used to determine the concentration of the analyte.

Figure 7A:
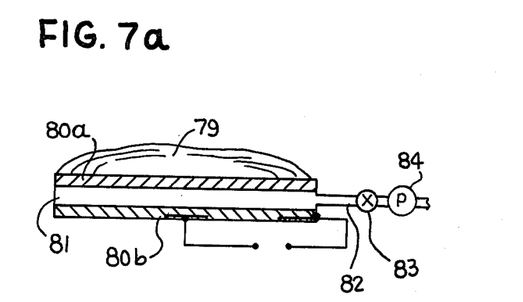
Figure 7B:
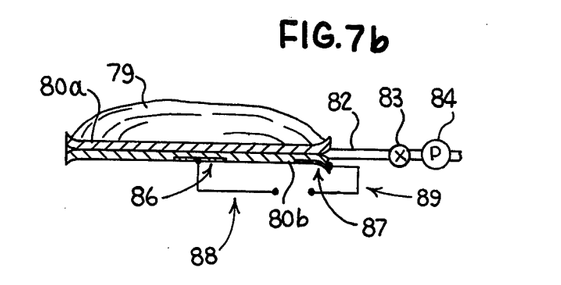

Referring now to FIGS. 7a, 7b and 7c, a further embodiment of the invention is shown. In this embodiment, diffusion between two respective layers 80a and 80b is maintained for a given period of time to effect a measurable reaction between sample analyte and reagent. The blood sample 79 is placed over porous layer 80a. The analytes contained in the plasma of the blood sample 79, diffuse into layer 80a until the layer is saturated. A barrier layer 81 of immiscible fluid is removed from between layers 80a and 80b via conduit 82, open valve 83 and pump 84. This causes layers 80a and 80b to contact each other, and the reagents in layer 80b to cross diffuse with the analyte(s) in layer 80a, as illustrated in FIG. 7b. The reaction between the analyte and reagent is monitored in layer 80b by means of attached electrodes 86 and 87 connected to wires 88 and 89, respectively. The cross-diffusion, as aforementioned, is maintained for a given period of time, thus, insuring a given aliquot of analyte will be reacted with a known amount of reagent. The diffusion is terminated by restoration of the barrier liquid 81 between the layers 80a and 80b, respectively, causing them to separate, as depicted in FIG. 7c.

The sample 79 need not be removed in this embodiment, because the reaction is monitored electrochemically after a controlled (time measured) diffusion. A precise aliquot is obtained because the diffusion can be very accurately controlled by means of reintroduction of the barrier layer 81.

Figure 8:
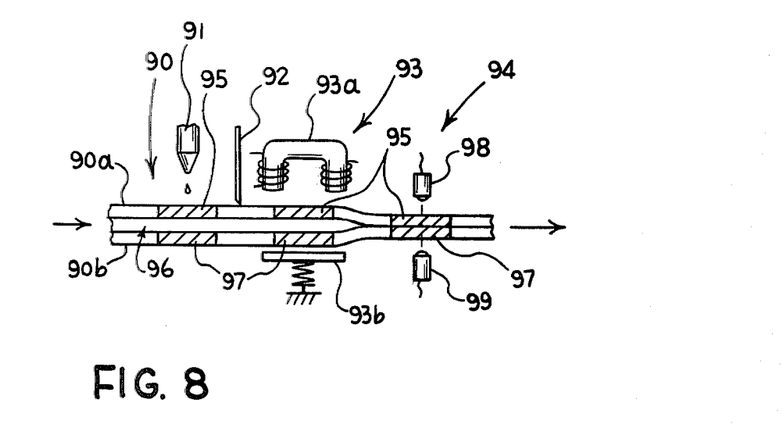
FIG. 8 shows a sectional view of an automated embodiment of the invention depicted in FIGS. 6a and 6b.

Referring to FIG. 8, an automated system for blood analysis is shown. A continuous web 90 is successively indexed past a blood dispenser 91, a wiper station 92, an electromagnetic contact station 93, and a readout station 94, respectively. The web 90 is composed of an upper layer 90a which has discrete sample receiving gel segments 95 of given volume. Layer 90a is separated by a fluid barrier 96 from a lower layer 90b having discrete reagent containing gel segments 97.

The plasma from the dispensed blood sample (station 91) diffuses into and saturates the gel 95 of layer 90a. After the gel 95 is saturated, the web is advanced to a wiper 92, which removes the excess blood from the surface of gel 95. Next, the gel 95 is indexed between an electromagnet 93a and a spring biased magnetizable plate 93b. When the electromagnet 93a is energized, it attracts the magnetizable plate 93b. This causes gels 95 and 97 to come into contact, thus displacing barrier fluid 96. Cross-diffusion will now take place between the gels causing a reaction between analyte and reagent. The web 90 is now advanced past a readout station 94 comprising a light source 98 and a colorimetric detector 99. The color intensity of the reaction is quantitatively related to the concentration of the analyte in the sample.

Figure 9:
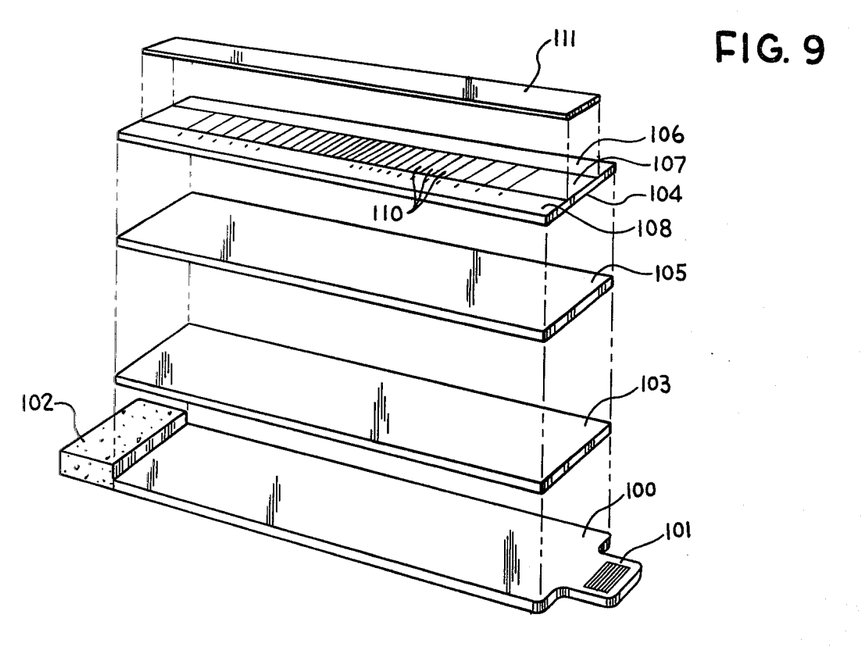
FIG. 9 illustrates an exploded view of an embodiment of the invention featuring a dip-stick apparatus.

Now referring to FIG. 9, a dip-stick embodiment of the present invention is shown in an exploded view. The dip-stick comprises a plastic base member 100 having a handle 101 at one end, and a fluid absorbing wick 102 on the other. The plastic base 100 supports a thin layer of reagent gel 103. A second sample receiving gel layer 104 sits within a thin support frame made of plastic or thin gasket material, not shown which separates and defines the gel compartments 110 and section 106 on top of the reagent gel 103. The reagent gel 103 and sample receiving gel 104 are separated by a barrier liquid layer 105. The sample receiving gel layer 104 is divided into three parts: (a) an exposed side section 106 of known volume which is designed to receive the fluid sample; (b) a center section 107 containing a graduated series of analyte containing compartments 110, each having a progressively higher concentration of the analyte under test; and (c) a side section 108 having a numerical designation beside each compartment 110 of section 107.

Section 107 is covered by a hard plastic piece 111. This plastic piece 111 prevents any analyte in the sample from entering compartments 110, and is also used to displace the barrier fluid layer 105 from between layers 103 and 104, respectively.

In use, the dip-stick is immersed into a fluid sample, such as whole blood (not shown). After the plasma of the blood sample has thoroughly saturated the side section 106 of layer 104, the remaining blood portion is removed from the surface of section 106. Next, the support 101 is placed on a flat surface, such as a table top, and the plastic piece 111 is pressed downwardly with the thumbs of the user. This causes the fluid barrier 105 to be displaced from between layers 103 and 104, respectively. The fluid 105 is caused to be absorbed by the wick 102.

Layers 103 and 104 are now in contact with each other resulting in the cross-diffusion of the analyte and reagent. The various compartments 110 in layer 104 will develop a progressive, graduated color pattern. Section 106 will develop a color indicative of the concentration of the analyte in the sample. When both sections 106 and 107 have color developed, the color of section 106 is compared with the closest color match of one of the compartments 110 of section 107. The numerical value of the analyte concentration is then read from the designation disposed opposite this compartment on section 108.

The immiscible barrier fluid presents a precise way of controlling diffusion across membranes or gels. Many possible modifications in the aforementioned apparatus will naturally occur to the trained practitioner of this art. For example, the gel or membrane layers containing the reagent may be covalently bound to the reagent so that cross-migration (diffusion) of the reagent will not occur. In such a case, only the analyte will diffuse into the reagent gel producing a color only in the reagent gel.

The barrier layer must be immiscible with the analyte, and may be either hydrophobic or hydrophilic, depending upon the nature of the analyte being analyzed.

Having thus described the invention, what is desired to be protected by Letters Patent is presented by the appended claims.

What is claimed is:

1. An apparatus for analyzing a whole blood sample, comprising:
   a first-thin film porous medium of a given predetermined volume for contact with said whole blood sample to be analyzed, a fluid component of said sample diffusing into said first porous medium;
   a second porous medium containing at least one reagent therein;
   a fluid barrier interposed between said first and second porous media to isolate said reagent and said fluid component;
   means for contacting said first porous medium with said second porous medium, to allow cross-diffusion therebetween, said contacting means including means for displacing said fluid barrier from between at least portions of opposing surfaces of said first and second media and cause said opposing surfaces to contact; and
   means to measure a reaction between said reagent and said fluid component in either of said first or second media.

2. The apparatus of claim 1, wherein said porous media comprise gel material.

3. The apparatus of claim 1, wherein said measuring means comprises a colorimeter.

4. The apparatus of claim 1, wherein said measuring means comprises a spectrophotometer.

5. The apparatus of claim 1, wherein said displacing means comprises a vacuum control means for providing a vacuum between said first and second media in order to displace said fluid barrier and to cause said opposing surfaces of said first and second media to contact.

6. The apparatus of claim 1, wherein said fluid barrier is a magnetic substance and said displacing means comprises magnetic means for displacing said magnetic substance and cause said opposing surfaces of said first and second media to contact.

7. The apparatus of claim 1, wherein said displacing means comprises means for pressing said first and second media toward each other to displace said fluid barrier and cause said opposing surfaces of said first and second media to contact.

8. An apparatus for analyzing a fluid sample for an analyte, comprising:
- a first porous medium for containing said analyte of said fluid sample;
- a second porous medium containing at least one reagent for reaction with said analyte of said fluid sample;
- a liquid barrier disposed between said first and second media to isolate said reagent from said analyte; and
- means for displacing said liquid barrier from between said first medium and said second medium to allow contact therebetween, whereby said analyte and said reagent can cross diffuse and react.

9. The apparatus of claim 8, wherein said barrier removing means comprises a pressure plate disposed adjacent said porous media for forcing said media into contact with each other, and simultaneously therewith, displacing said barrier from between said first and second media.

10. The apparatus of claim 8, wherein said displacing means defines a well disposed adjacent said media for catching said displaced liquid.

11. The apparatus of claim 8, further comprising a strip adjacent said first porous medium having a graduated series of standards to which said analyte-reagent reaction is compared.

12. The apparatus of claim 8, further comprising a substrate for supporting said first and second media.

13. The apparatus of claim 12, wherein said substrate has a hand-held portion on one end thereof, for dipping said first and second media into a receptacle containing said aqueous fluid sample.

14. The apparatus of claim 8, wherein said displacing means further comprises means for absorbing said displaced liquid.

15. The apparatus of claim 14, wherein said absorbing means comprises a porous wick.

16. A diffusion switch comprising:
- a first porous medium adapted to contain a first fluid for diffusion to a second porous medium;
- a second porous medium for receiving said first fluid when said second porous medium is in contact with said first porous medium;
- a second fluid disposed between said first porous medium and said second porous medium, said second fluid serving as a diffusion barrier between said first medium and said second medium; and
- means for displacing said second fluid from between said first medium and said second medium to allow contact therebetween, whereby diffusion of said first fluid can occur from said first medium to said second medium.

17. The diffusion switch of claim 16, further comprising means for restoring said second fluid between said first medium and said second medium after diffusion has occurred.

18. The diffusion switch of claim 16, wherein said first fluid is hydrophobic and said second fluid is hydrophilic.

19. The diffusion switch of claim 16, wherein said first fluid is hydrophilic and said second fluid is hydrophobic.

20. The diffusion switch of claim 16, wherein said second porous medium comprises at least one reagent which is reactive with said first fluid.

21. The diffusion switch of claim 16, wherein said first porous medium comprises a gel material.

22. The diffusion switch of claim 16, wherein said second porous medium comprises a gel material.

23. The diffusion switch of claim 16, wherein said fluid displacing means comprises a pressure control means.

24. The diffusion switch of claim 16, wherein said fluid displacing means comprises an electromagnetic control means.

25. The diffusion switch of claim 16, wherein said fluid displacing means comprises a vacuum control means.

26. The diffusion switch of claim 16, wherein said second fluid comprises a magnetic substance.

27. The diffusion switch of claim 26, wherein said fluid displacing means comprises a magnetic control means.

28. A diffusion switch comprising:
- a first porous medium adapted to contain a first fluid comprising a component for diffusion to a second porous medium;
- a second porous medium for receiving said component when said second porous medium is in contact with said first porous medium;
- a second fluid disposed between said first porous medium and said second porous medium, said second fluid serving as a diffusion barrier between said first medium and said second medium; and
- means for displacing said second fluid from between said first medium and said second medium to allow contact therebetween, whereby diffusion of said component can occur from said first medium to said second medium.

29. A method of performing a reaction with an analyte of a sample, comprising the steps of:
(a) diffusing said analyte into a first porous medium;
(b) contacting said first porous medium with a second porous medium to allow diffusion of said analyte into said second porous medium, said second porous medium having at least one first reagent for reaction with said analyte; and
(c) contacting said second porous medium with a third porous medium containing at least one second reagent, said contacting of at least two of said porous media comprising the displacement of a liquid from between said two media.

30. The method of claim 29, wherein said contacting steps (b) and (c) are performed sequentially.

31. The method of claim 29, wherein said contacting steps (b) and (c) are performed concurrently.

* * * * *